United States Patent
Burrows et al.

(10) Patent No.: US 9,460,265 B2
(45) Date of Patent: Oct. 4, 2016

(54) DATA-ENABLED PHARMACEUTICAL CONTAINER AND METHODS FOR USING SAME

(71) Applicant: DoseCue, LLC, Philadelphia, PA (US)

(72) Inventors: Mark Burrows, Philadelphia, PA (US); Neal Eckhaus, Rochester, NY (US); Donald Grube, Rochester, NY (US); George Christoffersen, Cherry Hill, NJ (US)

(73) Assignee: DoseCue, LLC, Philadelphia, PA (US)

( * ) Notice: Subject to any disclaimer, the term of this patent is extended or adjusted under 35 U.S.C. 154(b) by 356 days.

(21) Appl. No.: 14/042,767

(22) Filed: Oct. 1, 2013

(65) Prior Publication Data
US 2015/0095047 A1 Apr. 2, 2015

(51) Int. Cl.
*A61J 7/04* (2006.01)
*G06F 19/00* (2011.01)
*A61J 1/16* (2006.01)

(52) U.S. Cl.
CPC ............ *G06F 19/3462* (2013.01); *A61J 7/049* (2015.05); *A61J 7/0418* (2015.05); *A61J 7/0436* (2015.05); *A61J 1/16* (2013.01); *A61J 7/0454* (2015.05)

(58) Field of Classification Search
CPC .......... A61J 7/04; A61J 7/049; A61J 7/0418; A61J 7/0454; A61J 7/0436
USPC ....................................................... 221/15
See application file for complete search history.

(56) References Cited

U.S. PATENT DOCUMENTS

| | | | |
|---|---|---|---|
| 4,367,955 A * | 1/1983 | Ballew | A61J 7/0472 215/2 |
| 4,419,016 A | 12/1983 | Zoltan | |
| 4,434,903 A | 3/1984 | Cooke | |
| 4,448,541 A * | 5/1984 | Wirtschafter | A61J 7/0409 368/10 |
| 4,739,890 A | 4/1988 | Cooke | |
| 5,313,439 A | 5/1994 | Albeck | |
| 5,646,912 A | 7/1997 | Cousin | |
| 6,259,654 B1 * | 7/2001 | de la Huerga | A61J 7/0084 368/10 |
| 6,271,753 B1 | 8/2001 | Shukla | |
| 6,604,650 B2 | 8/2003 | Sagar | |

(Continued)

*Primary Examiner* — Timothy Waggoner
(74) *Attorney, Agent, or Firm* — Ward and Smith, P.A.; Ryan K. Simmons

(57) ABSTRACT

A data-enabled pharmaceutical container and methods for reminding at dose time, then tracking and communicating valid dose events and/or dose exception events are disclosed. Examples of dose exception events include, but are not limited to, missed doses, extra doses, early doses, and late doses. The data-enabled pharmaceutical container includes control electronics for processing and communicating information about valid dose events and/or dose exception events. For example, using a dose detection algorithm, a dose event is deemed valid based on (1) sensing the open state of the data-enabled pharmaceutical container (e.g., sensing that the closure is not present), (2) sensing a certain orientation or tilt of the data-enabled pharmaceutical container, and (3) sensing that the data-enabled pharmaceutical container is both opened and tilted simultaneously for a certain amount of time (e.g., a few seconds).

23 Claims, 16 Drawing Sheets

(56) References Cited

U.S. PATENT DOCUMENTS

| | | | |
|---|---|---|---|
| 7,362,660 B2* | 4/2008 | Hildebrandt | A61J 7/0481 221/2 |
| 7,554,434 B1 | 6/2009 | Gifford et al. | |
| 7,993,055 B2* | 8/2011 | Nurse | A61J 7/0481 368/244 |
| 2002/0026105 A1 | 2/2002 | Drazen | |
| 2002/0104848 A1* | 8/2002 | Burrows | A61J 7/0481 221/1 |
| 2002/0188182 A1 | 12/2002 | Haines et al. | |
| 2003/0216624 A1 | 11/2003 | Lin et al. | |
| 2004/0133305 A1 | 7/2004 | Jean-Pierre | |
| 2005/0267356 A1 | 12/2005 | Ramasubramanian et al. | |
| 2007/0097792 A1 | 5/2007 | Burrows et al. | |
| 2011/0227734 A1* | 9/2011 | Ortenzi | G08B 13/1436 340/568.1 |
| 2012/0056000 A1* | 3/2012 | Shores | A61J 7/0409 235/492 |

* cited by examiner

DATA-ENABLED PHARMACEUTICAL CONTAINER AND METHODS FOR USING SAME

RELATED PATENTS

U.S. Pat. No. 8,067,935, filed Jun. 5, 2008, entitled "System for sensing the opening and closing of a pharmaceutical container," which is incorporated by reference herein in its entirety.

FIELD OF THE INVENTION

The present invention generally relates to the field of medication adherence. In particular, the present invention is directed to a data-enabled pharmaceutical container and methods for reminding at dose time, then tracking and communicating valid dose events and/or dose exception events.

BACKGROUND

Outpatient prescription medication treatments are relied upon heavily for increased quality of life and lower lifetime healthcare costs. Medical experts have long held that taking at least 80% of a prescribed drug is required to achieve desired therapeutic outcomes and lower lifetime healthcare costs. For example, a patient who faithfully takes cholesterol-reducing medicine significantly reduces the likelihood of a coronary event that has attendant cost-intensive medical procedures and diminished quality of life. Outpatients strongly desire to avoid such events and hospital stays, yet only 20% of all outpatients take their prescription medicines according to doctor's instructions.

Increased medication adherence, also known as patient adherence, medication compliance, or patient compliance, benefits the healthcare system by vastly reducing patients' lifetime medical costs while increasing their therapeutic outcomes. Further, market research suggests that patients have a desire to comply, but will not take on the burden of any additional actions or otherwise change their behavior.

SUMMARY OF THE INVENTION

In one embodiment, the invention provides a data-enabled pharmaceutical container. The data-enabled pharmaceutical container may include a pharmaceutical container; and an electronics module configured for sensing and tracking dose events coupled to the pharmaceutical container. The pharmaceutical container may include a container body; a container neck; and a container closure, wherein the container body may be configured as a reservoir for holding a quantity of medication, the container neck may include an opening for dispensing the medication from the container body, and the container closure may be configured to secure the container neck opening. The medication may include pills, capsules, or caplets. The electronics module may include a housing and a printed circuit board (PCB) assembly housed therein, the PCB assembly may include a PCB; one or more indicators, one or more switches; and one or more sensors. The one or more sensors may include active and/or passive sensors. At least one of the sensors may be configured to sense one or more of a presence or absence of the container closure and an orientation or tilt of the pharmaceutical container. The electronics module may further include electrical components for processing data from the sensors with respect to a patient's predefined dosing regimen, and for storing and communicating data about doses taken, doses missed, extra doses, early doses, and/or late doses. The one of the one or more sensors may include a movable lever. The movable lever may extend through an opening in the housing and toward the container neck, wherein the movable lever may be part of a mechanism for sensing whether the container closure is present at or absent from the container neck. The movable lever may be configured such that when the container closure is present on the container neck an edge of the container closure is in contact with a tip of the movable lever causing the movable lever to be in a first position, and when the container closure is not present on the container neck the edge of the container closure does not contact the tip of the movable lever causing the movable lever to be in a second position. The one or more switches of the PCB assembly may include a momentary contact switch and wherein the movable lever in one of the first and second positions engages an actuator of the momentary contact switch. The container of movable lever and the momentary contact switch may provide the sensing mechanism for determining whether the container closure of pharmaceutical container is in an opened or closed state, wherein when the container closure is present and in contact with the tip of the movable lever, a portion of the movable lever is pushed against the actuator of the momentary contact switch, and the momentary contact switch is in one state, and when the container closure is not present and not in contact with the tip of the movable lever, the movable lever is not pushed against the actuator of the momentary contact switch, and the momentary contact switch is in another state. The electronics module may be coupled to the pharmaceutical container, such that there is no contact between the electronics module and the medication therein. The electronics module may be coupled to the container body using a sleeve, wherein the sleeve may affix the electronics module to the container body. The pharmaceutical container may include an integrated pharmaceutical container, wherein the pharmaceutical container comprises a compartment for housing the electronics module. The pharmaceutical container may further include a battery compartment. The electronics module may include control electronics including a communications interface; a processor; a real-time clock; a contact switch; a tilt sensor; and the one or more indicators. The processor may include data storage for storing one or more of a patient's dosing regimen; a dose detection algorithm; and actual dose data. The control electronics may be configured for providing a reminder at dose time, detecting valid dose events, and processing and communicating data about dose events and/or dose exception events. The at least one of the sensors may include a tilt sensor. The tilt sensor senses when the container body is in a tilted state exceeding a threshold angle from a first position. The threshold angle may be in the range of about 45° to about 90°. The tilt sensor may include any one of an on/off tilt sensor, an accelerometer, an inertial measurement unit (IMU), or an inclinometer. The sensing a valid dose event may require data input from at least two of the one or more switches and/or sensors to coincide with one another. The coinciding at least two data inputs from the one or more switches and/or sensors may include data input indicating the container closure is not present on the container neck and the container body is in a tilted state exceeding a threshold angle from a first position. The one or more indicators may include light-emitting diodes (LED). The electronics module may be further configured for providing a dose reminder and communicating valid dose events and/or dose exception events.

In another embodiment, the invention provides a method of determining a valid dose event using a data-enabled pharmaceutical container. The method may include providing a data-enabled pharmaceutical container; monitoring the data-enabled pharmaceutical container for pre-defined valid dose event criteria; determining whether the data-enabled pharmaceutical container has met the pre-defined criteria for the valid dose event; and recording the valid dose event upon determining the pre-defined criteria for the valid dose event is met. The data-enabled pharmaceutical container, may include a pharmaceutical container; and an electronics module configured for sensing and tracking dose events coupled to the pharmaceutical container, wherein the pharmaceutical container may include a container body; a container neck; and a container closure, wherein the container body may be configured as a reservoir for holding a quantity of medication, the container neck comprises an opening for dispensing the medication from the container body, and the container closure may be configured to secure the container neck opening, and wherein the electronics module may include a housing and a printed circuit board (PCB) assembly housed therein, the PCB assembly may include a PCB; one or more indicators, one or more switches; and one or more sensors. The determining of whether the data-enabled pharmaceutical container has met the pre-defined criteria for the valid dose event may include one or more of determining if the data-enabled pharmaceutical container is in an opened state, determining whether the data-enabled pharmaceutical container has met a defined tilt criteria, and determining whether the data-enabled pharmaceutical has met a defined time criteria. The pre-defined criterion for the valid dose event may include the data-enabled pharmaceutical container being in an opened state and the data-enabled pharmaceutical container exceeding a defined tilt threshold criterion for a defined period of time. The method may further include detecting, tracking, and communicating data regarding valid dose events and/or dose exception events. The monitoring of the data-enabled pharmaceutical container for pre-defined valid dose event criteria may include, the electronics module continuously monitoring the state of the one or more switches and sensors, and time of a real-time clock in relation to a patient's defined dosing regimen. The method may further include detecting, tracking, and communicating data regarding a patient's actual dose information.

In yet another embodiment, the invention provides a method of using a data-enabled pharmaceutical container for reminding at dose time, then tracking and communicating valid dose events and/or dose exception events. The method may include preparing the data-enabled pharmaceutical container for use; monitoring valid dose event criteria and medication adherence; determining whether a valid dose event has occurred; and recording actual dose event data. The preparing of the data-enabled pharmaceutical container for use may include one or more of programming a patient's dosing regimen into a processor of the data-enabled pharmaceutical container; loading updates into the processor of the data-enabled pharmaceutical container; retrieving stored dose event data; setting or resetting a real-time clock of the data-enabled pharmaceutical container; checking diagnostics of the data-enabled pharmaceutical container; filling the data-enabled pharmaceutical container with medication; and labeling the data-enabled pharmaceutical container. The monitoring of valid dose event criteria and medication adherence may include the processor receiving and interpreting data from one or more of the patient's dosing regimen; a dose detection algorithm; the real-time clock; whether and when valid dose events occur and whether they are in compliance with/adherent to dosing instructions stored in the patient's dosing regimen. The data-enabled pharmaceutical container may include one or more indicators capable of being monitored by the patient. The one or more indicators may be one or more of visual and audible. The one or more indicators may be configured to indicate to the patient at least one of, time to take a dose, a dose has been missed, and time for a prescription refill. The method may further include transmitting data from the data-enabled pharmaceutical container to an external computing device using a communications interface. The method may further include following an actual dose event, deactivating any previously activated indicators and activating an applicable indicator according to the patient's dosing regimen and recording the actual dose event data. The data from the data-enabled pharmaceutical container may be transmitted to one or more of the patient, caretaker, and an authorized party via the communications interface. If the recorded actual dose event is a missed dose event according to the patient's dosing regimen the one or more indicators indicate a missed dose, and if the recorded actual dose event is a valid dose event according to the patient's dosing regimen the one or more indicators indicate a taken dose, and the applicable actual dose event is recorded. The method may further include determining whether a prescription refill is needed based on a number of valid dose events as compared to the recorded actual dose data and the patient's dosing regimen. If it is determined a prescription refill is needed the one or more indicators may indicate a prescription refill is needed. A prescription refill notice may be sent to one or more of the patient, a pharmacy, and any other caretaker or authorized party via a communications interface.

BRIEF DESCRIPTION OF THE DRAWINGS

Figure 1:
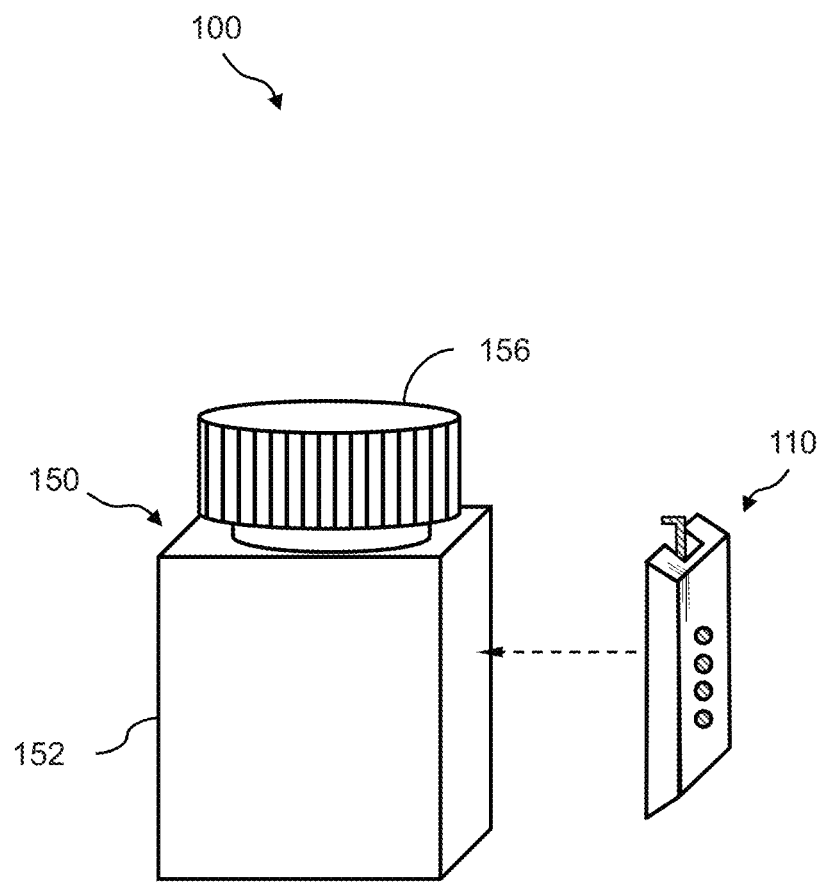
Figure 2:
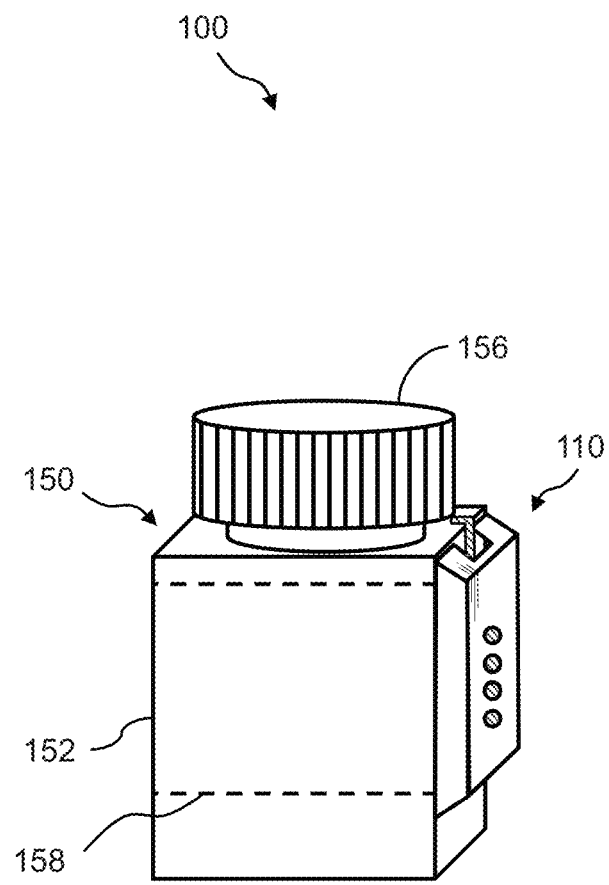
Figure 3:
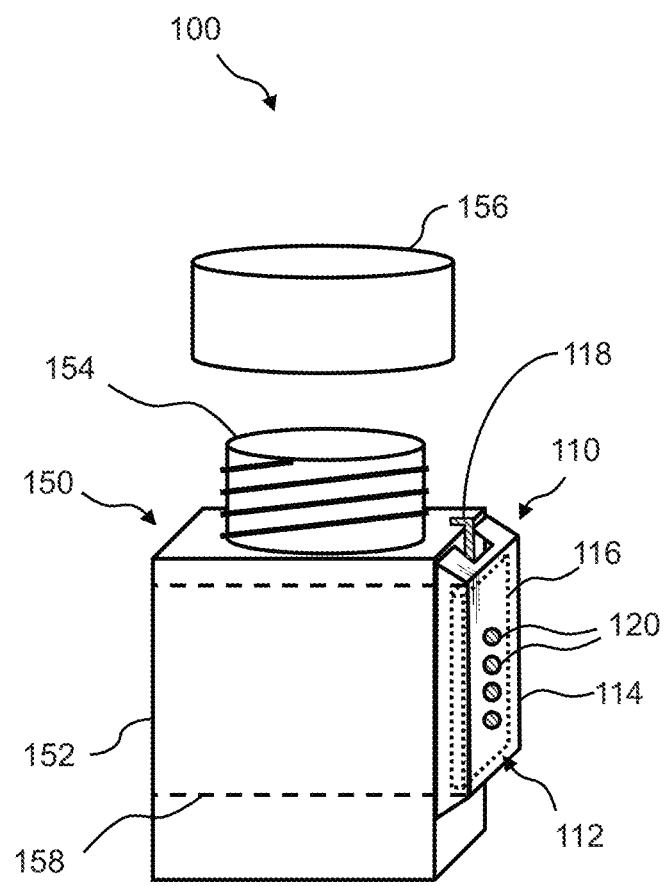
Figure 4:
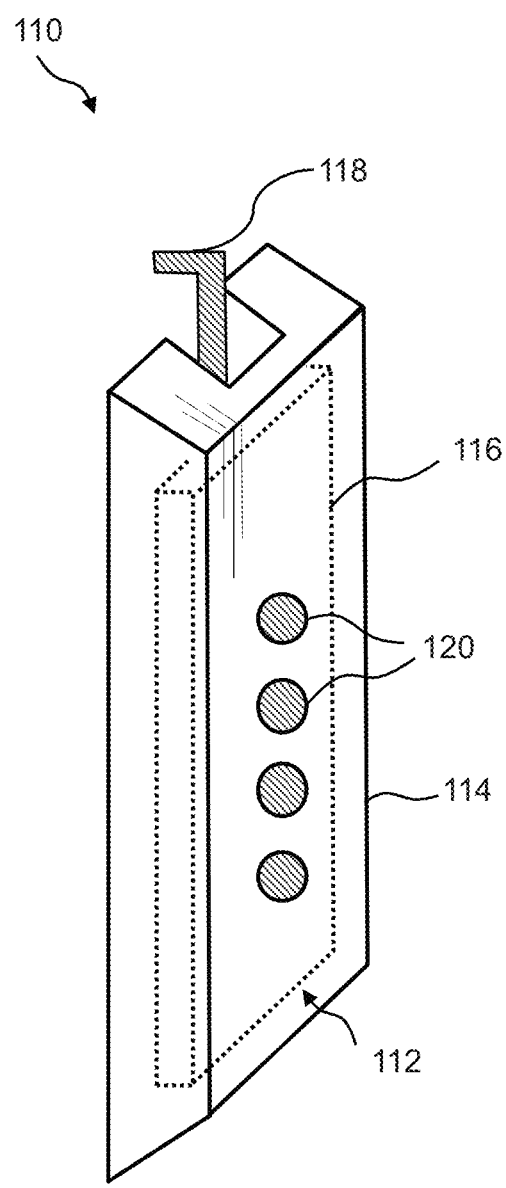
Figure 5:
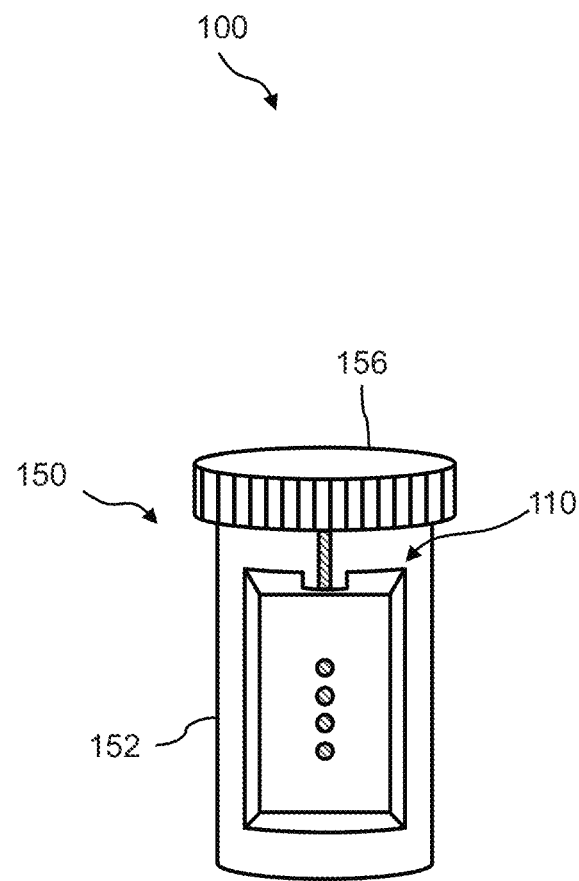
Figure 6:
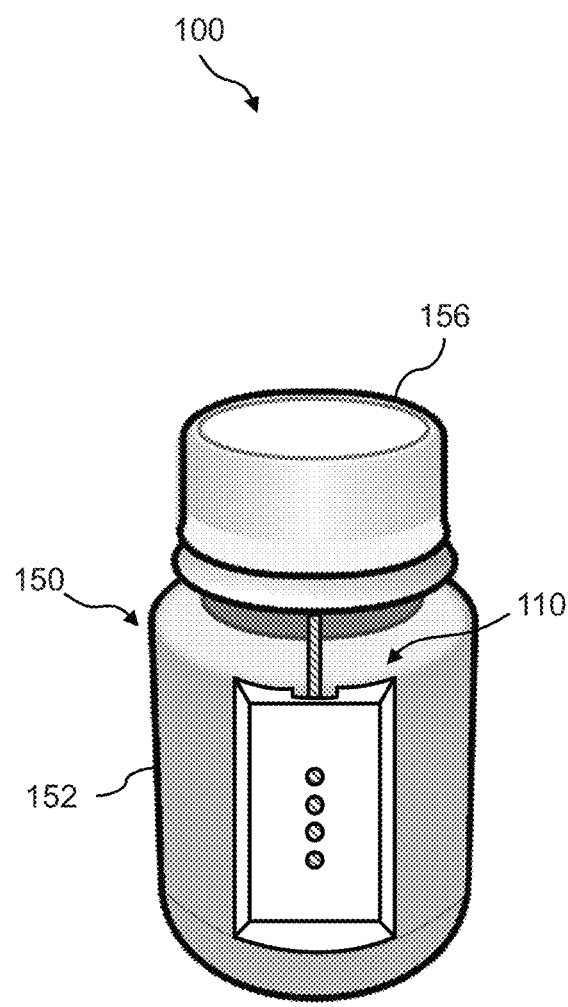
Figure 7:
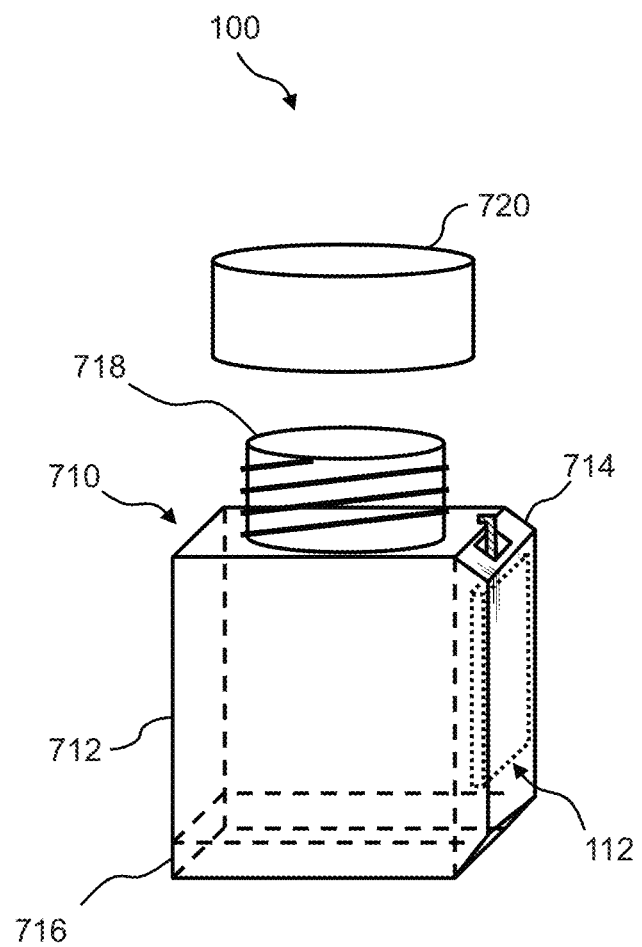
Figure 8:
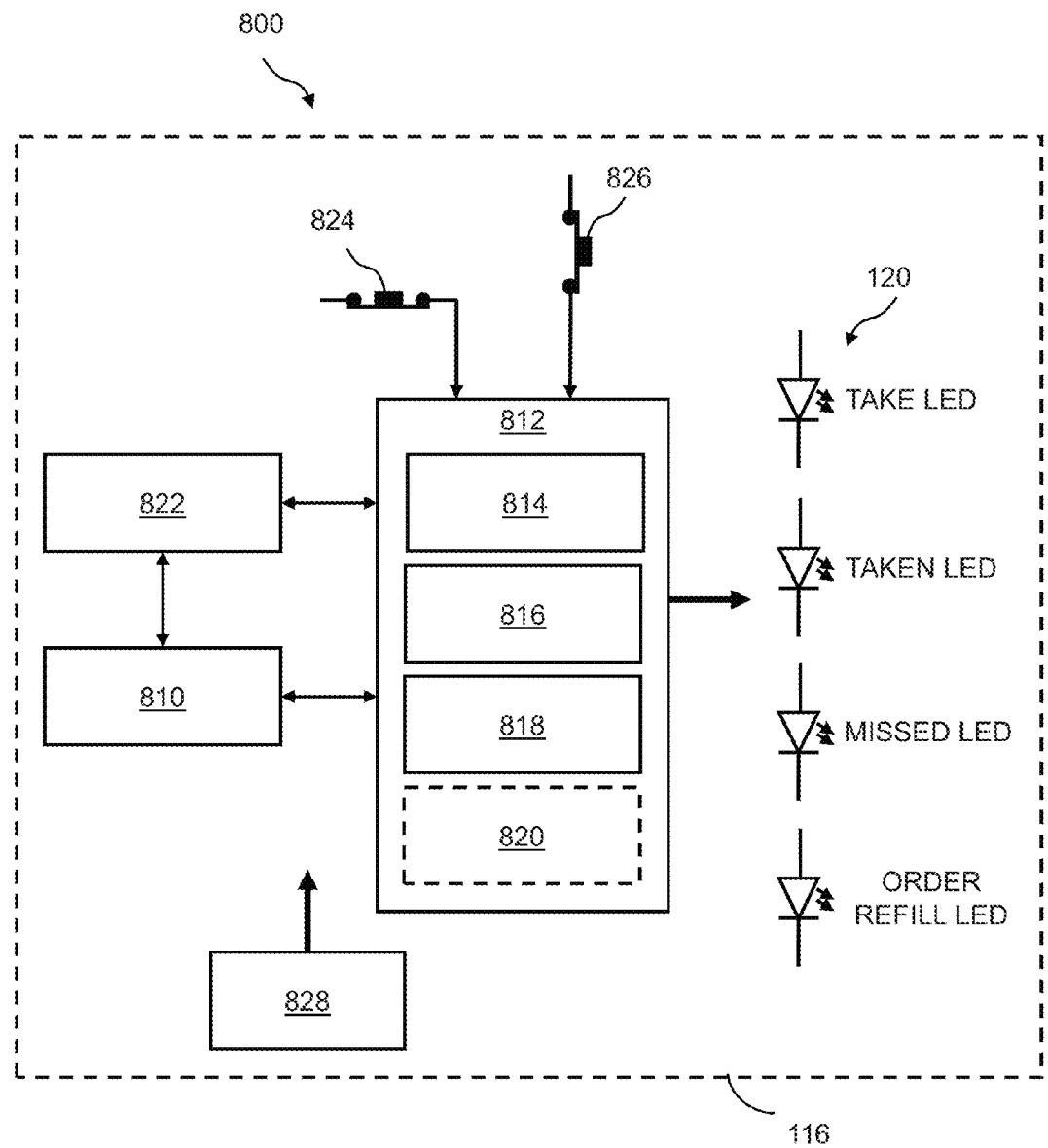
Figure 9:
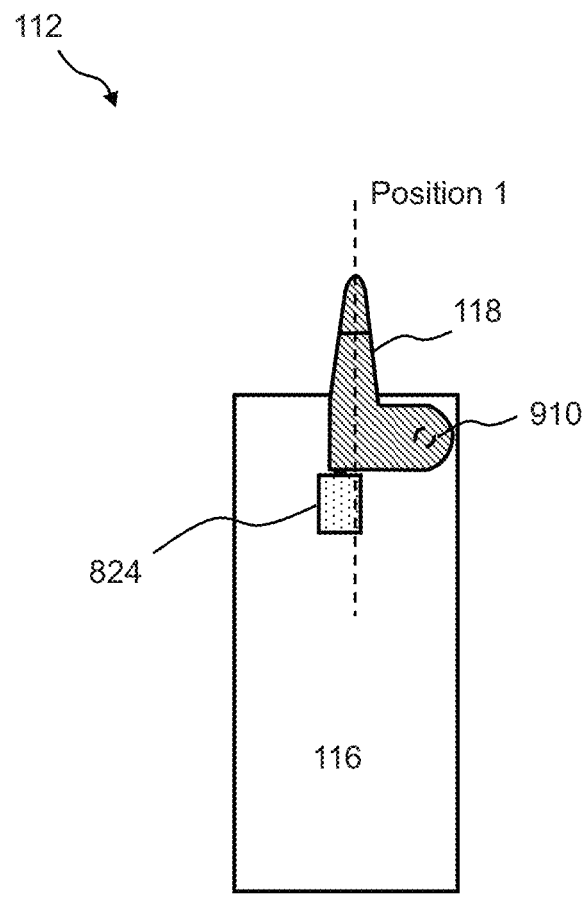
Figure 10:
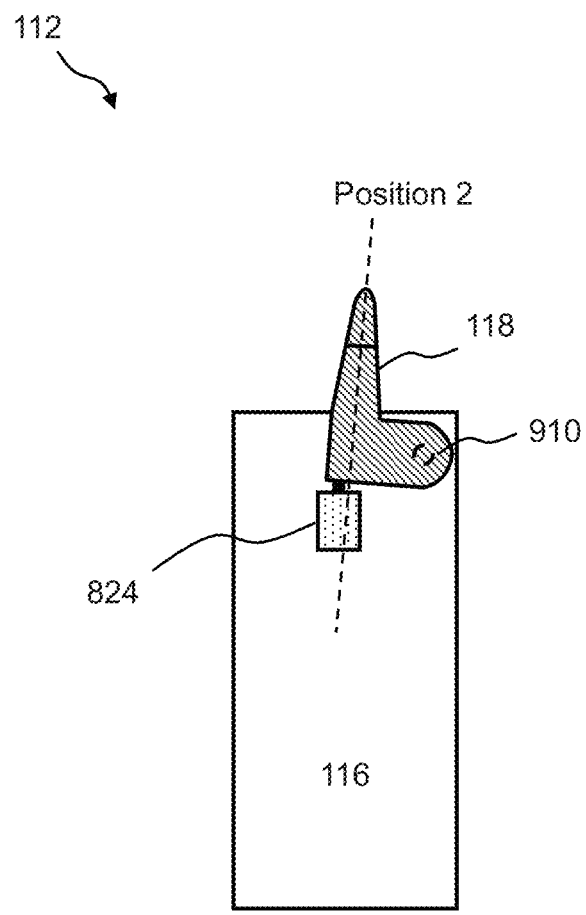
Figure 11:
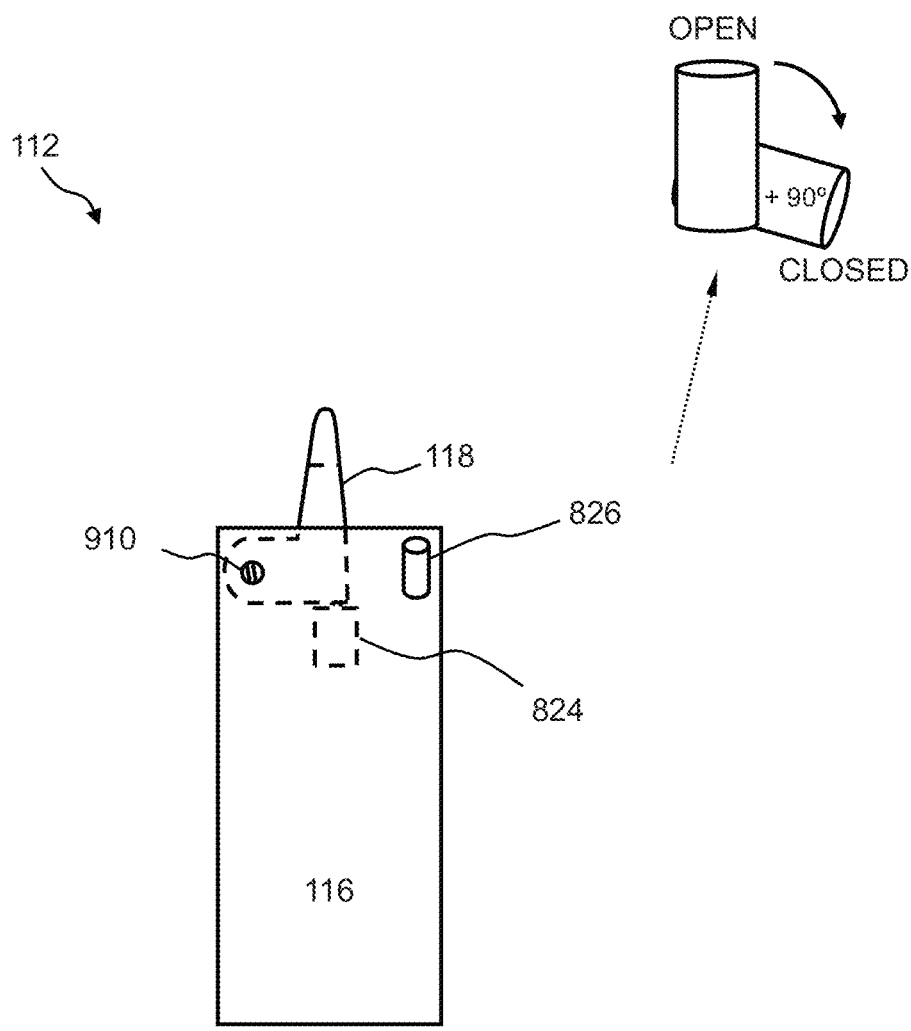
Figure 12A:
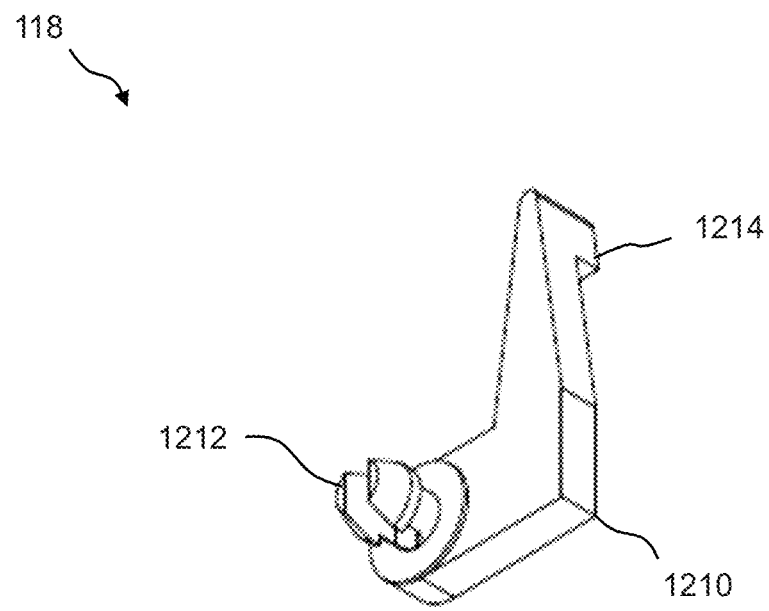
Figure 12B:
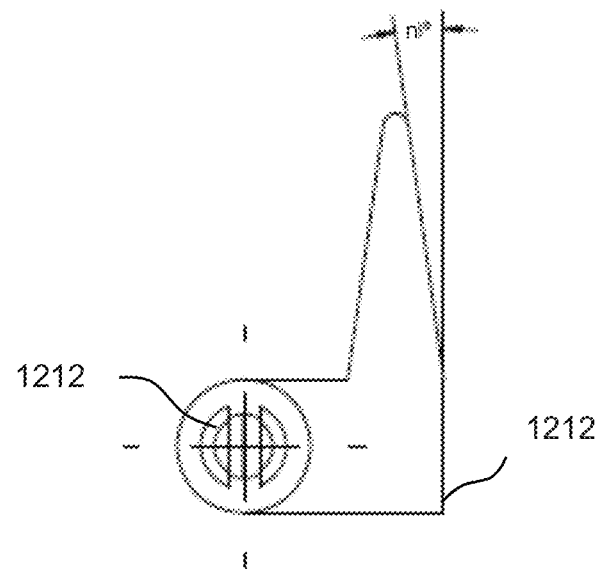
Figure 13:
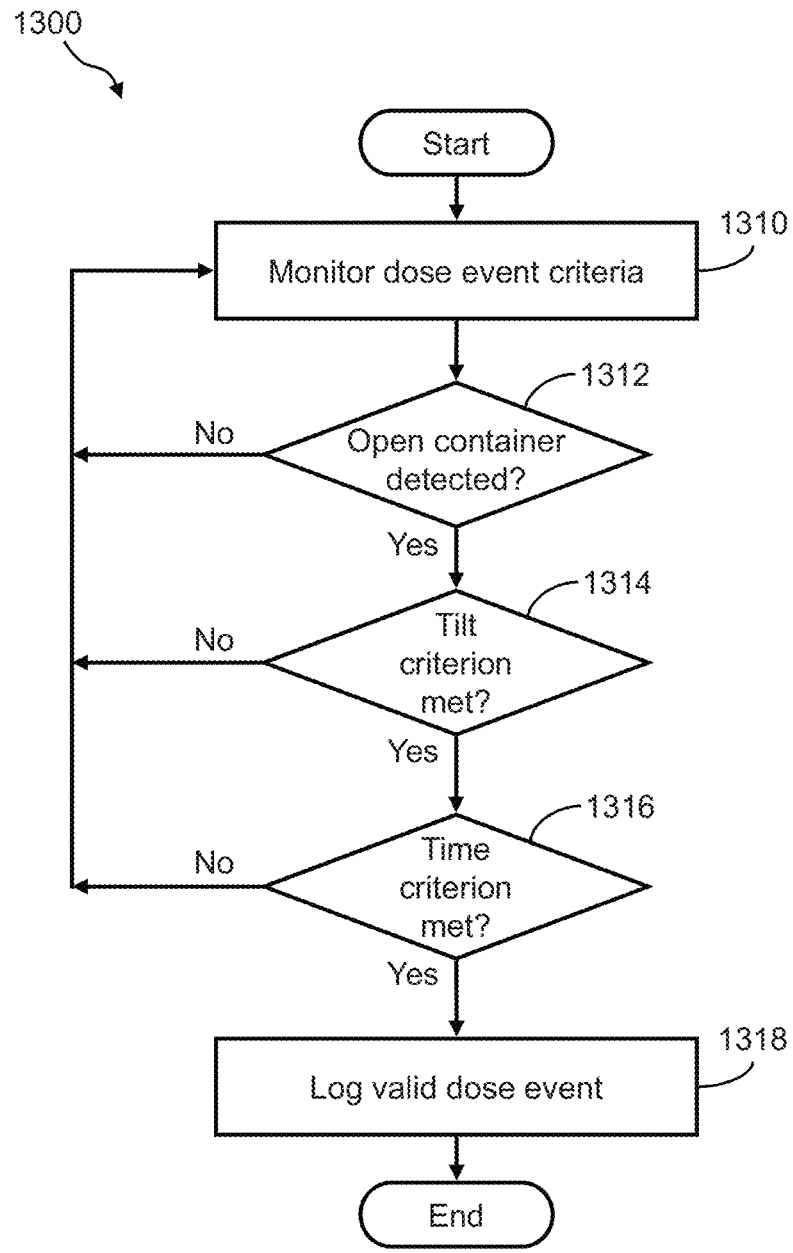
Figure 14:
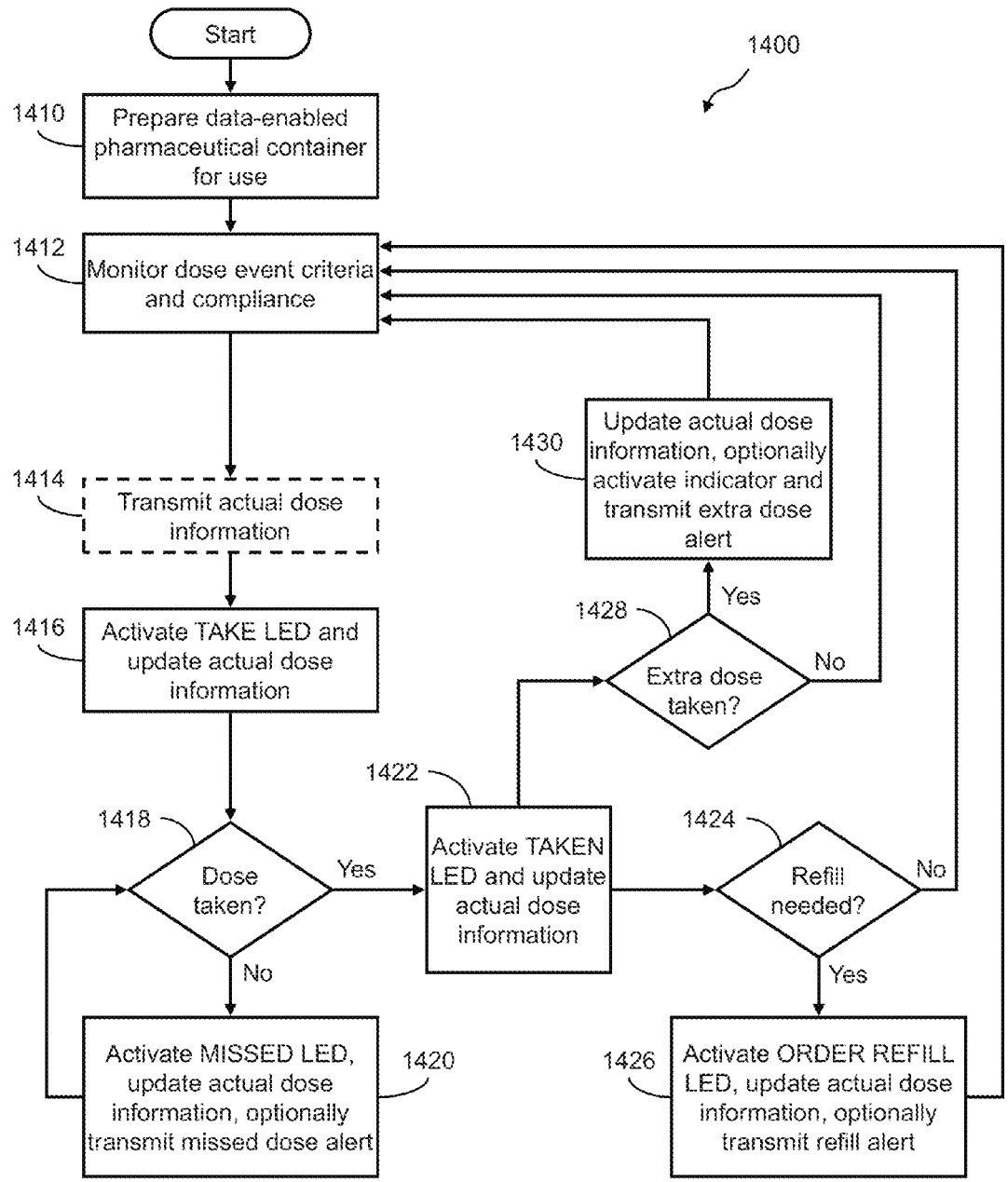
Figure 15:
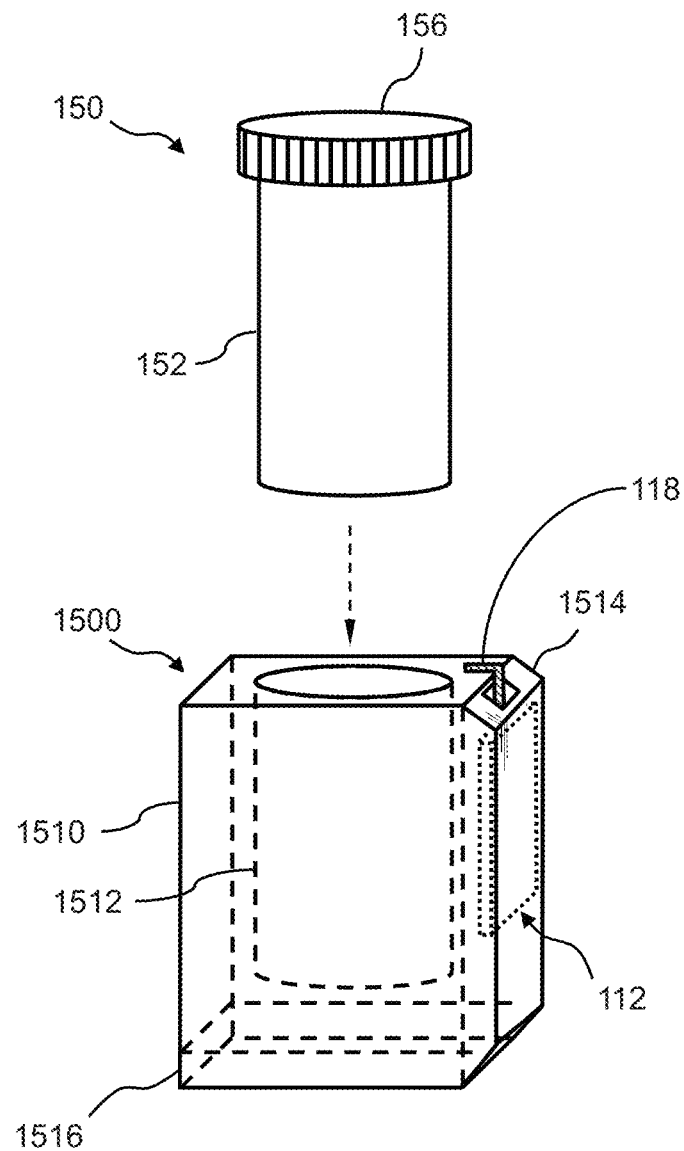
Figure 16:
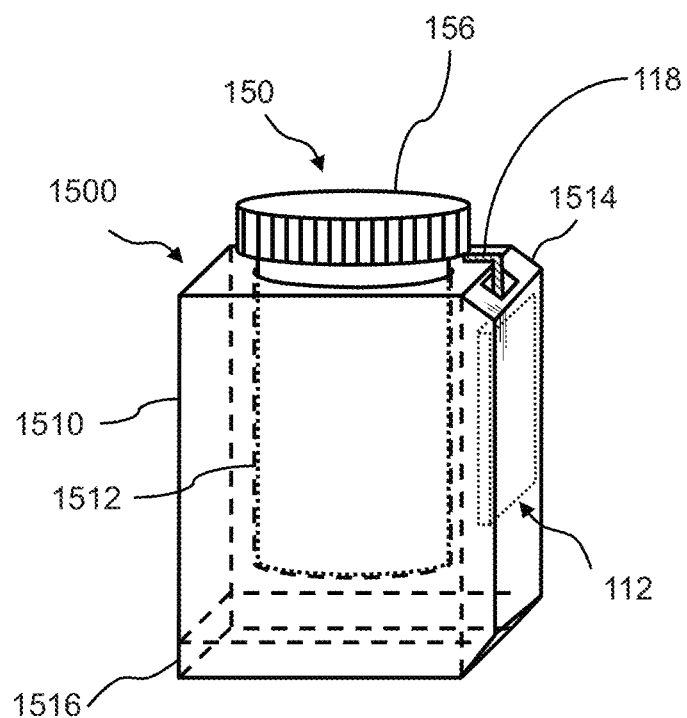

Having thus described the presently disclosed subject matter in general terms, reference will now be made to the accompanying Drawings, which are not necessarily drawn to scale, and wherein:

FIG. 1, FIG. 2, and FIG. 3 illustrate perspective views of a data-enabled pharmaceutical container for reminding at dose time, then tracking and communicating valid dose events and/or dose exception events;

FIG. 4 illustrates a perspective view of an electronics module of the presently disclosed data-enabled pharmaceutical container;

FIG. 5 and FIG. 6 illustrate perspective views of other examples of the presently disclosed data-enabled pharmaceutical container;

FIG. 7 illustrates a perspective view of an example of the presently disclosed data-enabled pharmaceutical container that includes an integrated pharmaceutical container;

FIG. 8 illustrates a block diagram of an example of control electronics of the presently disclosed data-enabled pharmaceutical container;

FIG. 9 and FIG. 10 illustrate plan views of the side of a PCB assembly of the presently disclosed data-enabled pharmaceutical container, wherein the PCB assembly is oriented toward the container body and showing a lever thereof in two different positions, respectively;

FIG. 11 illustrates a plan view of the side of the PCB assembly of the presently disclosed data-enabled pharmaceutical container, wherein the PCB assembly is oriented away from the container body;

FIG. 12A and FIG. 12B illustrate a perspective view and a back view, respectively, of an example of the lever of the presently disclosed data-enabled pharmaceutical container;

FIG. 13 illustrates a flow diagram of an example of a method of determining a valid dose event using the presently disclosed data-enabled pharmaceutical container;

FIG. 14 illustrates a flow diagram of an example of a method of operation of the presently disclosed data-enabled pharmaceutical container; and FIG. 15 and FIG. 16 are perspective views and an example of a data-enabled pharmaceutical sleeve into which a conventional pharmaceutical container is installed, wherein together the data-enabled pharmaceutical sleeve and the conventional pharmaceutical container provide substantially the same functionality as the presently disclosed data-enabled pharmaceutical container.

DETAILED DESCRIPTION

The presently disclosed subject matter provides a data-enabled pharmaceutical container and methods for reminding at dose time, then tracking and communicating valid dose events and/or dose exception events. Examples of dose exception events include, but are not limited to, missed doses, extra doses, early doses, and late doses. In some embodiments, the presently disclosed subject matter provides an electronics module that can be attached to any conventional pharmaceutical container, thereby forming the data-enabled pharmaceutical container. In other embodiments, the data-enabled pharmaceutical container is formed of a custom pharmaceutical container in which the electronics is built directly into the container. Namely, the custom pharmaceutical container includes one compartment for holding medication and another compartment for housing the electronics, wherein the electronics is not in contact with the contents of the container.

The presently disclosed subject matter also provides a data-enabled pharmaceutical sleeve into which a conventional pharmaceutical container is installed, wherein the sleeve includes the electronics. Together, the data-enabled pharmaceutical sleeve and the conventional pharmaceutical container provide substantially the same functionality as the data-enabled pharmaceutical container.

The electronics module of the data-enabled pharmaceutical container includes circuitry for reminding at dose time, then detecting valid dose events, as well as for processing and communicating information about valid dose events and/or dose exception events. For example, using a dose detection algorithm, a dose event is deemed valid based on (1) sensing the open state of the data-enabled pharmaceutical container (e.g., sensing that the closure is not present), (2) sensing a certain orientation or tilt (e.g., more than 90 degrees from vertical, or past horizontal) of the data-enabled pharmaceutical container, and (3) sensing that the data-enabled pharmaceutical container is both opened and tilted more than 90 degrees simultaneously for a certain amount of time (e.g., a few seconds).

An aspect of the data-enabled pharmaceutical container is that it may be used to increase patient adherence with respect to dosing regimens while requiring no additional actions or otherwise changed behavior by the patient, such as programming, record keeping, or decanting of medication from one container into another.

Another aspect of the data-enabled pharmaceutical container is that the sensing mechanisms are reliable and are sufficiently low cost to be practical for use in commercial product applications.

Yet another aspect of the data-enabled pharmaceutical container is that records of digital information about dose events and/or dose exception events (e.g., missed, extra, early, and late doses) are automatically generated and stored thereon, wherein the digital information can be used to determine periodically or continuously whether the prescribed dosing regimen is being followed.

Still another aspect of the data-enabled pharmaceutical container is that it includes a communications interface for wired or wireless communication with an external computing device.

FIG. 1, FIG. 2, and FIG. 3 illustrate perspective views of a data-enabled pharmaceutical container 100 for reminding at dose time, then tracking and communicating valid dose events and/or dose exception events. The data-enabled pharmaceutical container 100 includes an electronics module 110 that is attached or otherwise affixed to a pharmaceutical container 150. The pharmaceutical container 150 can be substantially any pharmaceutical container in use today. In the example shown in FIG. 1, FIG. 2, and FIG. 3, the pharmaceutical container 150 includes a container body 152 and a container neck 154. The container body 152 is a reservoir for holding, for example, a quantity of pills, capsules, caplets, and the like, which, for example, are prescribed to a patient (not shown) according to a certain dosing regimen. The container neck 154 is the opening for dispensing medication from the container body 152. In one example, the container neck 154 may be threaded for receiving a closure 156, which may be a screw-type cap. The pharmaceutical container 150 (e.g., the container body 152, the container neck 154, and the closure 156) may be formed of any suitably rigid, lightweight, and food-safe material, such as molded high-density polyethylene (HDPE), e.g., molded plastic. Other examples of the pharmaceutical container 150 are shown with reference to FIG. 5 and FIG. 6.

The electronics module 110 may include active and passive electrical components for sensing the presence or absence of the closure 156, for sensing the orientation or tilt of the pharmaceutical container 150, for processing these sensing mechanisms with respect to the patient's dosing regimen, and for storing and communicating information about doses taken, doses missed, extra doses, early doses, and/or late doses. More details of the electronics module 110 are shown and described with reference to FIG. 4 and FIG. 8.

Referring now to FIG. 1, the data-enabled pharmaceutical container 100 is shown with the electronics module 110 apart from the pharmaceutical container 150, e.g., prior to assembly. Referring now to FIG. 2 and FIG. 3, the data-enabled pharmaceutical container 100 is shown with the electronics module 110 attached to the pharmaceutical container 150, e.g., after assembly. In FIG. 1, FIG. 2, and FIG. 3, the pharmaceutical container 150 may be a container that has a substantially square or rectangular cross-section. Therefore, the housing of the electronics module 110 may be attached to one side of the pharmaceutical container 150, which may be flat. FIG. 2 shows the data-enabled pharmaceutical container 100 in the closed state, meaning that the closure 156 may be secured atop the container neck 154 of the container body 152. By contrast, FIG. 3 shows the data-enabled pharmaceutical container 100 in the opened state, meaning that the closure 156 is not secured atop the container neck 154 of the container body 152.

Additionally, FIG. 3 and FIG. 4 show more details of the physical instantiation of the electronics module 110. For example, the electronics module 110 includes a printed circuit board (PCB) assembly 112 that may be enclosed in a housing 114, wherein the shape and size of the housing 114 can vary according to the shape and size of the pharmaceutical container 150. The housing 114 can be formed, for example, of the same material that the pharmaceutical container 150 is formed of (e.g., molded plastic). The PCB assembly 112 further includes a PCB 116 on which the control electronics (see FIG. 8) is implemented, a movable lever 118, one or more of the indicators 120, and various other switches and sensors (again see FIG. 8).

The lever 118 extends through an opening in the housing 114 and toward the container neck 154 as shown. The lever 118 is part of the mechanism for sensing whether the closure 156 is present at or absent from the container neck 154, meaning whether the data-enabled pharmaceutical container 100 is closed or opened. Namely, when the closure 156 is present (e.g., when the data-enabled pharmaceutical container 100 is closed) the edge of the closure 156 comes into contact with the tip of the lever 118, which causes the lever 118 to be in one position. However, when the closure 156 is not present (e.g., when the data-enabled pharmaceutical container 100 is opened) the edge of the closure 156 is not in contact with the tip of the lever 118, which causes the lever 118 to be in a different position. The lever 118 is used in conjunction with a momentary contact switch (see FIG. 8). More details of the lever 118 are shown and described with reference to FIG. 9 through FIG. 12D.

The housing 114 and the PCB assembly 112 are provided on the outside of the container body 152, such that there is no contact with the contents inside of the container body 152. In one example, the housing 114 and the PCB assembly 112 are affixed to the container body 152 using a sleeve or label 158, wherein the sleeve or label 158 is wrapped around both the container body 152 and the housing 114 so that the housing 114 is substantially hidden from view. The sleeve or label 158 is formed of any material suitable to be printed on and suitable to last the lifetime of the data-enabled pharmaceutical container 100.

The pharmaceutical container 150 of the data-enabled pharmaceutical container 100 is not limited to a four-sided type of container with a threaded neck and threaded cap. Any type of pharmaceutical container can be used in the data-enabled pharmaceutical container 100. FIG. 5 shows another example of a pharmaceutical container 150 in which the container body 152 has a cylindrical shape and in which the closure 156 is a snap-fitted cap. In this example, the housing 114, the PCB assembly 112, and the lever 118 are sized and shaped accordingly such that the snap-fitted closure 156 can be in contact with the tip of the lever 118 when the snap-fitted closure 156 is present (e.g., when the data-enabled pharmaceutical container 100 is closed). FIG. 6 shows yet another example of a pharmaceutical container 150 that is substantially the same as the pharmaceutical container 150 shown in FIG. 1, FIG. 2, and FIG. 3 except that the container body 152 is cylindrical rather than four-sided. Again, the housing 114, the PCB assembly 112, and the lever 118 are sized and shaped accordingly and such that the screw-type closure 156 can be in contact with the tip of the lever 118 when the screw-type closure 156 is present (e.g., when the data-enabled pharmaceutical container 100 is closed).

In another embodiment of the data-enabled pharmaceutical container 100, instead of using a separate electronics module 110 with an existing pharmaceutical container 150, the data-enabled pharmaceutical container 100 can include a customized container that includes at least a first compartment for holding medication and a second compartment for housing the PCB assembly 112, wherein the PCB assembly 112 is not in contact with the medication in the first compartment. For example, FIG. 7 shows an example of the data-enabled pharmaceutical container 100 that includes an integrated pharmaceutical container 710. The integrated pharmaceutical container 710 includes a medication compartment 712, an electronics compartment 714, and optionally a battery compartment 716.

The medication compartment 712 is a reservoir for holding, for example, a quantity of pills, capsules, caplets, and the like, which are prescribed to a patient (not shown) according to a certain dosing regimen. Atop the medication compartment 712 is a container neck 718, which is the opening for dispensing medication from the medication compartment 712. In this example, the container neck 718 is threaded for receiving a closure 720, which is a screw-type cap. The integrated pharmaceutical container 710 may be formed of any suitably rigid, lightweight, and food-safe material, such as molded HDPE, e.g., molded plastic.

The electronics compartment 714 is used to house the PCB assembly 112, wherein the PCB assembly 112 is not in contact with the medication in the medication compartment 712. The battery compartment 716 is used to house one or more batteries (not shown) for supplying power to the PCB assembly 112, wherein the batteries are not in contact with the medication in the medication compartment 712. An access door or panel (not shown) can be provided in the electronics compartment 714 for accessing the PCB assembly 112. Similarly, an access door or panel (not shown) can be provided in the battery compartment 716 for accessing the one or more batteries therein.

This embodiment of the data-enabled pharmaceutical container 100 is not limited to that shown in FIG. 7. The integrated pharmaceutical container 710 shown in FIG. 7 is exemplary only. The integrated pharmaceutical container 710 can take other shapes and sizes, such as, but not limited to, the shapes and sizes shown in FIG. 5 and FIG. 6.

FIG. 8 illustrates a block diagram of an example of control electronics 800 of the electronics module 110 of the data-enabled pharmaceutical container 100 for reminding at dose time, then detecting valid dose events, as well as for processing and communicating information about valid dose events and/or dose exception events (e.g., missed, extra, early, and late doses). The control electronics 800 is circuitry that is implemented on the PCB 116. In this example, the control electronics 800 includes a communications interface 810; a processor 812 that further includes the patient's dosing regimen 814, a dose detection algorithm 816, actual dose information 818, and optionally a security component 820; a real-time clock 822; a momentary contact switch 824; a tilt sensor 826; and the one or more indicators 120. The components of the control electronics 800 are powered by one or more batteries 828. Each of the batteries 828 can be any standard cylindrical battery, such as quadruple-A, triple-A, or double-A, or a battery from the family of button cell and coin cell batteries. A specific example of a battery 828 may be the CR2032 coin cell 3-volt battery.

The communications interface 810 may be any wired and/or wireless communication interface for connecting to a network (not shown) and by which information may be exchanged with other devices connected to the network. Examples of wired communication interfaces may include, but are not limited to, USB ports, RS232 connectors, RJ45 connectors, Ethernet, and any combinations thereof. Examples of wireless communication interfaces may include, but are not limited to, an Intranet connection, Internet, ISM, Bluetooth® technology, Wi-Fi, Wi-Max, IEEE 802.11 technology, radio frequency (RF), Infrared Data Association (IrDA) compatible protocols, Local Area Networks (LAN), Wide Area Networks (WAN), Shared Wireless Access Protocol (SWAP), any combinations thereof, and other types of wireless networking protocols. Examples of information facilitated by the communications interface 810 include the transmission of the dosing regimen 814 and the actual dose information 818. Other examples of information facilitated by the communications interface 810 is the transmission of a "missed dose" alert, a "refill" alert, and an "extra dose" alert to the patient, to a caretaker, or to any other authorized party.

The processor 812 is used to manage the overall operations of the data-enabled pharmaceutical container 100 with respect reminding at dose time, then tracking and communicating valid dose events and/or dose exception events (e.g., missed, extra, early, and late doses). The processor 812 can be any standard controller or microprocessor device that is capable of executing program instructions. A certain amount of data storage (not shown) may be associated with the processor 812. In one example, the processor 812 is the PIC18LF14K50 Microcontroller, available from Microchip Technology, Inc (Chandler, Ariz.).

Using the communications interface 810, a patient's dosing regimen 814 can be loaded into the processor 812. The dosing regimen 814 can be any information about the patient's prescribed medication and dosing regimen. In one example, the patient's dosing regimen 814 indicates one 50-mg dose per day of levothroxine. In another example, the patient's dosing regimen 814 indicates two 50-mg doses daily (e.g., one dose every 12 hours) of levothroxine. In yet another example, the patient's dosing regimen 814 indicates three 50-mg doses daily of levothroxine (e.g., one dose upon waking, one mid-day dose, and one dose at bedtime).

The dose detection algorithm 816 that is programmed into the processor 812 is used to detect valid dose events. For example, a dose event is deemed valid based on (1) sensing the open state of the data-enabled pharmaceutical container 100 (e.g., sensing that the closure 156 is not present), (2) sensing a certain orientation or tilt (e.g., greater than 90 degrees from vertical, or past horizontal) of the data-enabled pharmaceutical container 100, and (3) sensing that the data-enabled pharmaceutical container 100 is both opened and tilted simultaneously for a certain amount of time (e.g., a few seconds). Using the aforementioned criteria, incidental movement of the data-enabled pharmaceutical container 100, such as the container falling over or being jostled in a computer bag or a purse, will not register by the dose detection algorithm 816 as a valid dose event.

With respect to sensing the open state of the data-enabled pharmaceutical container 100 (e.g., sensing that the closure 156 is not present), the lever 118 shown in FIG. 1 through FIG. 7 and shown in FIG. 9 through FIG. 12D is engaged with the actuator (e.g., pushbutton) of the momentary contact switch 824. Together, the lever 118 and the momentary contact switch 824 provide the sensing mechanism for determining whether the data-enabled pharmaceutical container 100 is opened or closed. When the closure 156 is present and in contact with the tip of the lever 118, a portion of the lever 118 is pushed against the actuator of the momentary contact switch 824, and the momentary contact switch 824 is in one state (e.g., closed), as shown in FIG. 9. By contrast, when the closure 156 is not present and therefore not in contact with the tip of the lever 118, the lever 118 is not pushed against the actuator of the momentary contact switch 824, and the momentary contact switch 824 is in another state (e.g., open), as shown in FIG. 10. In one example, the momentary contact switch 824 is a side-actuated micro-switch, such as the SDS005 side-actuated detect switch, available from ITT Corporation (White Plains, N.Y.). Accordingly, the state of the momentary contact switch 824 is one input of the dose detection algorithm 816 that is used for detecting valid dose events.

The data-enabled pharmaceutical container 100 is not limited to using the lever 118 and the momentary contact switch 824 for sensing whether the data-enabled pharmaceutical container 100 is opened or closed. Other mechanisms can be used, such as, but not limited to, the mechanisms described with reference to U.S. Pat. No. 8,067,935, filed Jun. 5, 2008, entitled "System for sensing the opening and closing of a pharmaceutical container," which is incorporated herein in its entirety. The '935 patent describes multiple embodiments of mechanisms for sensing the opening and closing of pharmaceutical containers. In particular, The '935 patent describes sensing mechanisms that trigger an automatic, built-in, electronic dosage reminder and open/close event logging operation while requiring no additional actions or otherwise changed behavior by the patient, in order to increase patient compliance with dosing regimens. In one embodiment, the sensing mechanism includes two electrical conductors that have no electrical connection therebetween when the closure is not present on the container and a bridge conductor in the closure that provides an electrical connection therebetween when the closure is tightened onto the container. In this example embodiment, the state of the two electrical conductors may be monitored in order to sense a container opening and closing event.

The tilt sensor 826 is used for sensing orientation or tilt of the data-enabled pharmaceutical container 100. A tilt sensor can measure the tilting in often two axes of a reference plane in two axes. In one example, the tilt sensor 826 is the SQ-SEN-390 on/off tilt sensor, available from SignalQuest, Inc (Lebanon, N.H.). The SQ-SEN-390 on/off tilt sensor acts like a position sensitive switch that is normally closed when below horizontal and normally open when above horizontal. An example of the tilt sensor 826 is shown in FIG. 11. With respect to the data-enabled pharmaceutical container 100, when the container body 152 is tilted beyond horizontal, e.g. past 90 degrees, the state of the tilt sensor 826 indicates that the container body 152 is in a position to potentially dispense (dump out) an oral dose form, such as a pill or capsule. Accordingly, the state of the tilt sensor 826 is another input of the dose detection algorithm 816 that is used for detecting valid dose events.

The data-enabled pharmaceutical container 100 is not limited to using the SQ-SEN-390 on/off tilt sensor for sensing orientation or tilt. Other mechanisms can be used for sensing tilt, such as, but not limited to, an accelerometer, an inertial measurement unit (IMU), and an inclinometer. Further, the data-enabled pharmaceutical container 100 is not limited to sensing orientation past 90 degrees. Less tilt than 90 degrees can be detected as needed with the above noted mechanisms for sensing tilt for specific uses, such as liquids, which may be dispensed from full containers with, for example, 45 degrees of tilt.

With respect to sensing that the data-enabled pharmaceutical container 100 is both opened and tilted simultaneously for a certain amount of time (e.g., a few seconds), the internal clock of the processor 812 or the real-time clock 822 can be used. For example, upon sensing both that the closure 156 is not present and a tilt below horizontal, the internal clock of the processor 812 or the real-time clock 822 is used to measure the amount of time that both conditions are simultaneously present. If both conditions are present at the same time for, for example, about 3 seconds, then the dose detection algorithm 816 logs the date and time of a valid dose event in the actual dose information 818. Accordingly, the time of both conditions being present is yet another input of the dose detection algorithm 816 that is used for detecting valid dose events. Any valid dose events that are detected via dose detection algorithm 816 are logged in the actual dose information 818. For example, the date and time of the dose event is logged in the actual dose information 818. More details of an example of a method of detecting a valid dose event are described with reference to FIG. 13.

Additionally, the processor 812 and/or the dose detection algorithm 816 can be programmed to compare valid dose events that are detected to information stored in the patient's dosing regimen 814. In so doing, it can be determined whether the prescribed dosing regimen is being followed. Namely, using the patient's dosing regimen 814, it can be determined whether doses have been taken on time, whether doses have been missed, whether extra doses have been taken, whether early doses have been taken, and whether late doses have been taken. Additionally, using the patient's dosing regimen 814, the processor 812 and/or the dose detection algorithm 816 can be used to activate reminder indicators and any other types of indicators. Namely, the real-time clock 822 provides a calendar and time of day function that can be used with the dosing regimen 814 in order to determine whether doses have been taken on time, whether doses have been missed, whether extra doses have been taken, whether early doses have been taken, and whether late doses have been taken, and to generate reminders. An example of the real-time clock 822 is the S-35390A, 2-wire CMOS real-time clock, available from Seiko Instruments, Inc (Torrance, Calif.).

The security component 820 in the processor 812 can be any software module that is used to perform any security functions with respect to keeping the contents of, for example, the dosing regimen 814 and the actual dose information 818 secure. For example, the security component 820 may use standard security techniques, such as encryption, secure hashtags (or hash tags), and the like. For example, the security component 820 can be used to decrypt the dosing regimen 814, which may be received encrypted. Additionally, the security component 820 can be used to encrypt the actual dose information 818 when transmitted via communications interface 810. However, the use of encryption in the data-enabled pharmaceutical container 100 is optional.

The one or more indicators 120 are used to convey information to the patient or caretaker in response to the information processed via processor 812 and/or the dose detection algorithm 816. Further, the time-stamped states of any of the indicators 120 can also be logged in the actual dose information 418. In one example, the indicators 120 are light-emitting diode (LED) devices. For example, four indicators 120 may be provided—a green "TAKE" LED, a light green "TAKEN" LED, a red "MISSED" LED, and a yellow "ORDER REFILL" LED. Openings (not shown) can be provided in the housing 114 and/or in the sleeve or label 158 of the data-enabled pharmaceutical container 100 that allow the indicators 120 to be visible. Further, TAKE, TAKEN, MISSED, and ORDER REFILL can be printed on the sleeve or label 158 corresponding to the four indicators 120.

The green "TAKE" LED is used for prompting the user to take the prescribed dose of medication. For example, the information contained within the dosing regimen 814 may indicate a patient should take one dose at 4:00 pm daily. When the real-time clock 822 indicates the current time to be about 4:00 pm, the processor 812 activates the "TAKE" LED. In another example, if the dosing regimen 814 indicates 2 doses daily, 12 hours apart, then the "TAKE" LED may be activated about 12 hours after the previously detected valid dose event.

Upon detecting a valid dose event via dose detection algorithm 816, the "TAKE" LED is deactivated and the light green TAKEN" LED is activated. Namely, the "TAKEN" LED indicates that a valid dose event has occurred as detected via dose detection algorithm 816. For example, if all criteria of the dose detection algorithm 816 are met, the processor 812 activates the "TAKEN" LED. After the valid dose event is detected, the "TAKEN" LED may remain activated (e.g., continues to flash) for some period of time (e.g., an hour or until the next dose time).

The red "MISSED" LED indicates a user has not taken the dose of medication in accordance to the dosing regimen 814. Using the real-time clock 822, the processor 812 may be programmed to activate the "MISSED" LED, for example, one hour past the scheduled dose time. For example, the information contained within the dosing regimen 814 may indicate a patient should take one dose at 4:00 pm daily. In this example, when the real-time clock 822 indicates the current time is 5:00 pm and a dose event has not recently been detected via dose detection algorithm 816, the processor 812 activates the "MISSED" LED. The "MISSED" LED may remain activated for a predetermined period of time (e.g., 1 hour) or until the "TAKE" LED is next activated. Additionally, using the communications interface 810, a "missed dose" alert can be transmitted to the patient, caretaker, or any other authorized party.

The yellow "ORDER REFILL" LED indicates the bottle is nearly out of medication and a prescription refill is needed. For example a patient's dosing regiment may require one dose per day for 30 days. Therefore, an initial fill of medication is 30 pills. The total number of pills contained within the data-enabled pharmaceutical container 100 (e.g., 30 pills) is indicated in the dosing regimen 814. The processor 812 can count the number of valid dose events logged in the actual dose information 818 and determine how many doses presently remain in the data-enabled pharmaceutical container 100. In addition to dose count, the processor 812 uses real-time clock 822 to verify that, for example, at least 25 days have passed since the last refill (for a 30-day prescription), as health insurance companies typically will not authorize monthly refills until 25 days have passed since the last refill (for a 30-day prescription). In another example, for a 90-day prescription, the time period may be 85 days. Once the number of doses is nearly depleted (e.g., 5 doses remaining) and the prescribed number of days have passed (e.g., 25 days or 85 days), the processor 812 activates the "ORDER REFILL" LED to indicate that a refill is needed. Additionally, using the communications interface 810, a "refill" alert can be transmitted to the patient, caretaker, or any other authorized party.

FIG. 9 and FIG. 10 illustrate plan views of the side of the PCB assembly 112 that is oriented toward the container body 152 and showing the lever 118 in two different positions. Namely, FIG. 9 shows the position of the lever 118 when the closure 156 is secured on the container neck 154 and pushing against the tip of the lever 118. In so doing, a portion of the lever 118 presses against the actuator of the momentary contact switch 824. By contrast, FIG. 10 shows the position of the lever 118 when the closure 156 is not present and therefore not pushing against the tip of the lever 118. In this state, the lever 118 is not pressed against the actuator of the momentary contact switch 824. FIG. 9 corresponds to the data-enabled pharmaceutical container 100 in the closed state. FIG. 10 corresponds to the data-enabled pharmaceutical container 100 in the opened state. The lever 118 moves about a pivot point 910. Together, the lever 118 and the momentary contact switch 824 provide the sensing mechanism for determining whether the data-enabled pharmaceutical container 100 is opened or closed.

Further to the example, FIG. 11 shows a plan view of the side of the PCB assembly 112 that is oriented away from the container body 152. Like FIG. 9, FIG. 11 corresponds to the data-enabled pharmaceutical container 100 in the closed state. Also shown in FIG. 11 is an example of the tilt sensor 826. However, the tilt sensor 826 is not limited to mounting on this side of the PCB 116. The tilt sensor 826 can be mounted on either side of the PCB 116.

FIG. 12A and FIG. 12B illustrate a perspective view and a back view, respectively, of an example of the lever 118. The lever 118 is formed of any suitably rigid, lightweight, and food-safe material, such as molded HDPE, e.g., molded plastic. The lever 118 may be made by, for example, injection molding. For example, the lever 118 is a substantially L-shaped member that includes an elbow 1210. One end of the L-shaped member may include a snap-fitting 1212 for securing the lever 118 to the PCB 116 in a pivoting fashion. Namely, the snap-fitting 1212 may be designed to be press-fitted into a hole in the PCB 116 and provides the pivot point 910 shown in FIG. 9, FIG. 10, and FIG. 11. The other end of the L-shaped member may include a protrusion 1214, which is the tip of the lever 118 that comes into contact with the closure 156 when in use. The lever 118 can be modified in any manner to allow the lever to negotiate the shoulder or shoulders of the container body 152 of the data-enabled pharmaceutical container 100. Namely, to be positioned under the closure 156 in order to toggle from one position to another depending on whether the data-enabled pharmaceutical container 100 is opened or closed. More particularly, the shape of the lever 118 can be tailored to correspond to the shape of the pharmaceutical container with which it is used as long as the tip of the lever 118 can come into contact with the closure thereof when closed.

FIG. 13 illustrates a flow diagram of an example of a method 1300 of determining a valid dose event using the data-enabled pharmaceutical container 100. The method 1300 may include, but is not limited to, the following steps.

At a step 1310, the processor 812 and/or the dose detection algorithm 816 monitor dose event criteria in order to detect valid dose events, track valid dose events, and communicate information about valid dose events and/or dose exception events. For example, the processor 812 and/or the dose detection algorithm 816 continuously monitor the state of the momentary contact switch 824, the state of the tilt sensor 826, the calendar date and time of the real-time clock 822; all in relation to the patient's dosing regimen 814.

At a decision step 1312, the processor 812 and/or the dose detection algorithm 816 determine whether the data-enabled pharmaceutical container 100 is opened, meaning whether the closure 156 is not secured to the data-enabled pharmaceutical container 100. Namely, the state of the momentary contact switch 824 indicates whether the closure 156 is secured or not secured to the data-enabled pharmaceutical container 100. In one example, if the momentary contact switch 824 is a normally open momentary contact switch, when the closure 156 is present and pressed against the tip of the lever 118, the momentary contact switch 824 is actuated and in the closed state. In this example, the momentary contact switch 824 in the closed state means that the data-enabled pharmaceutical container 100 is closed. By contrast, when the closure 156 is not present and not pressed against the tip of the lever 118, the momentary contact switch 824 is not actuated and in the open state. In this example, the momentary contact switch 824 in the open state means that the data-enabled pharmaceutical container 100 is opened. If it is determined that the data-enabled pharmaceutical container 100 is opened, the method 1300 proceeds to a step 1314. However, if it is determined that the data-enabled pharmaceutical container 100 is not opened, then the method 1300 returns to step 1310.

At a decision step 1314, the processor 812 and/or the dose detection algorithm 816 determine whether the tilt criterion of the data-enabled pharmaceutical container 100 has been met for a valid dose event. In one example the tilt criterion is greater than 90 degrees from vertical, or past horizontal. Namely, the state of the tilt sensor 826 indicates whether the data-enabled pharmaceutical container 100 is tilted enough to cause a pill or capsule to dispense from the container body 152. In one example, when the tilt sensor 826 is oriented substantially vertical its switch is open, which means that the data-enabled pharmaceutical container 100 is not tilted enough to cause a pill or capsule to dispense from the container body 152. By contrast, when the tilt sensor 826 is oriented greater than 90 degrees from vertical or past horizontal its switch is closed, which means that the data-enabled pharmaceutical container 100 is tilted enough to cause a pill or capsule to dispense from the container body 152. If it is determined that the tilt criterion of the data-enabled pharmaceutical container 100 has been met for a valid dose event, the method 1300 proceeds to a step 1316. However, if it is determined that the tilt criterion of the data-enabled pharmaceutical container 100 has not been met for a valid dose event, then the method 1300 returns to step 1310.

At a decision step 1316, the processor 812 and/or the dose detection algorithm 816 determine whether the time criterion of the data-enabled pharmaceutical container 100 has been met for a valid dose event. For example, upon sensing both that the data-enabled pharmaceutical container 100 is opened in step 1312 and that the tilt criterion is met in step 1314, the internal clock of the processor 812 or the real-time clock 822 is used to measure the amount of time that both conditions are simultaneously present. If both conditions are present at the same time for a predetermined amount of time, then the method 1300 proceeds to step 1318. The predetermined amount of time can be from about 2 seconds to about 5 seconds in one example, or is about 3 seconds in another example. However, if both conditions are not met at the same time for the prescribed length of time, then a valid dose event is not detected and the method 1300 returns to step 1310.

At a step 1318, a valid dose event is logged. Any valid dose events that are detected via dose detection algorithm 816 are logged in the actual dose information 818. For example, the date and time of the dose event is logged in the actual dose information 818.

FIG. 14 illustrates a flow diagram of an example a method 1400 of operation of the data-enabled pharmaceutical container 100. Namely, the method 1400 is a method of using the data-enabled pharmaceutical container 100 for reminding at dose time, then tracking and communicating valid dose events and/or dose exception events (e.g., missed, extra, early, and late doses). The method 1400 may include, but is not limited to, the following steps.

At a step 1410, the data-enabled pharmaceutical container 100 is prepared for use. For example, using the communications interface 810, a medical or pharmaceutical professional, or other qualified party, may connect, either wired and/or wirelessly, the data-enabled pharmaceutical container 100 to a computer (not shown) for programming and exchange of information between the computer and the data-enabled pharmaceutical container 100. For example, using the communications interface 810, the patient's dosing regimen 814 may be loaded into the processor 812, updates may be loaded into the dose detection algorithm 816, the real-time clock 822 may be set or reset, the health status of battery 828 may be checked, and the like. Further, the data-enabled pharmaceutical container 100 is filled with the prescribed medication, labeled, and physically conveyed to the patient for use. The method 1400 proceeds to step 1412.

At a step 1412, the processor 812 and/or the dose detection algorithm 816 monitor dose event criteria and medication adherence continuously or at specified intervals. For example, the processor 812 receives and interprets information from the dosing regimen 814, the dose detection algorithm 816, the real-time clock 822, whether and when valid dose events occur and whether they are in compliance with/adherent to prescribed dosing instructions stored in the dosing regimen 814. Further, at any time, the patient can visually monitor the indicators 120 to see whether any action is required, such as whether it is time to take a dose, whether a dose has been missed, whether it is time for a prescription refill, and the like. The method 1400 proceeds to step 1414.

At an optional step 1414, encrypted or unencrypted the actual dose information 818 is transmitted to an external computing device using the communications interface 810. Namely, at any time during the method 1300, any information at the data-enabled pharmaceutical container 100 can be interrogated using the communications interface 810. The method 1400 proceeds to step 1416.

At a step 1416, any previously activated indicators 120 are deactivated, the "TAKE" LED is activated according to the dosing regimen 814, and this event is logged in the actual dose information 818. Optionally, using the communications interface 810, a "take dose" alert can be transmitted to the patient or any other caretaker or authorized party that it is time to take the dose. The method 1400 proceeds to step 1418.

At a decision step 1418, it is determined whether a valid dose event has occurred according to the method 1300. If it is determined that a valid dose event has occurred, the method 1400 proceeds to step 1422. However, if it is determined that a valid dose event has not occurred within the prescribed period of time (e.g., within ±2 hours of the prescribed time), then the method 1400 proceeds to step 1420.

At a step 1420, any previously activated indicators 120 are deactivated, the "MISSED" LED is activated, and this event is logged in the actual dose information 818. Optionally, using the communications interface 810, a "missed dose" alert can be transmitted to the patient or any other caretaker or authorized party that the dose has been missed. The method 1400 returns to step 1418.

At a step 1422, once a valid dose event has been detected according to the method 1300, any previously activated indicators 120 are deactivated, the "TAKEN" LED is activated, and this event is logged in the actual dose information 818. Optionally, using the communications interface 810, a "dose taken" alert can be transmitted to the patient, the pharmacy, or any other caretaker or authorized party. The method 1400 proceeds to both step 1424 and step 1428.

At a decision step 1424, it is determined whether a prescription refill is needed. For example, the processor 812 can count the number of valid dose events logged in the actual dose information 818 and determine how many doses presently remain in the data-enabled pharmaceutical container 100. In addition to dose count, the processor 812 uses real-time clock 822 to verify that, for example, at least 25 days have passed since the last refill (for a 30-day prescription), as health insurance companies typically will not authorize monthly refills until 25 days have passed since the last refill (for a 30-day prescription). In another example, for a 90-day prescription, the time period may be 85 days. If the processor 812 determines that the number of doses is nearly depleted (e.g., 5 doses remaining) and the prescribed number of days have passed (e.g., 25 days or 85 days), then method a prescription refill is needed and the method 1400 proceeds to step 1426. However, if the processor 812 determines that the number of doses is not nearly depleted (e.g., greater than 5 doses remaining) or that the prescribed number of days have not passed, then a prescription refill is not needed and the method 1400 returns to step 1412.

At a step 1426, any previously activated indicators 120 are deactivated, the "ORDER REFILL" LED is activated, and this event is logged in the actual dose information 818. Optionally, using the communications interface 810, a "refill" alert can be transmitted to the patient, the pharmacy, or any other caretaker or authorized party. The method 1400 returns to step 1412.

At a decision step 1428, it is determined whether an extra dose event has occurred according to the method 1300 and according to the dosing regimen in the patient's dosing regimen 814. If it is determined that an extra dose event has occurred, the method 1400 proceeds to step 1430. However, if it is determined that an extra dose event has not occurred with respect to the dosing regimen in the patient's dosing regimen 814, then the method 1400 returns to step 1412.

At a step 1430, the extra dose event is logged in the actual dose information 818. Optionally, using the communications interface 810, an "extra dose" alert can be transmitted to the patient, the pharmacy, or any other caretaker or authorized party. Optionally, the electronics module 110 can include an EXTRA DOSE LED that is activated in this step. The method 1400 returns to step 1412.

Table 1 below shows an example of a record of data in the actual dose information 818 that can be compiled using the method 1300 of FIG. 13 and/or the method 1400 of FIG. 14. In the example shown in Table 1, the record of data is for one calendar day.

TABLE 1

Example record of data in the actual dose information 418 for July 12, 2013

Patient Name: John Doe
Patient Address: 487 Elm St, Scranton, PA 18505
RX # 0569790-07365
Medication: LEVOTHROXINE
Dose: Two 50-mg doses daily

| Timestamp Data | Event Data |
| --- | --- |
| 12-Jul-2013; 06:35:15.2 | "TAKE" LED activated |
| 12-Jul-2013; 07:35:15.2 | "MISSED" LED activated |
| 12-Jul-2013; 07:51:15.7 | Valid dose event detected, "MISSED" LED deactivated, "TAKEN" LED activated |
| 12-Jul-2013; 08:51:15.7 | "TAKEN" LED deactivated |
| 12-Jul-2013; 19:51:15.7 | "TAKE" LED activated |
| 12-Jul-2013; 20:34:15.4 | Valid dose event detected, "TAKE" LED deactivated, "TAKEN" LED activated |
| 12-Jul-2013; 21:34:15.4 | "TAKEN" LED deactivated |

While the example shown in Table 1 is a record of data is for one calendar day, the actual dose information 818 can include any number of records, for any number of days. For example, Table 2 below shows an example of a summary report for a 30-day period, wherein the summary report is compiled using information in the actual dose information 818. Table 2 also shows the percent medication adherence for the patient for the 30-day period.

TABLE 2

Example summary report 118 for a 30-day period

Patient Name: John Doe
Patient Address: 487 Elm St, Scranton, PA 18505
RX # 0569790-07365
Medication: LEVOTHROXINE
Start: June 15, 2013
Duration: 30 days
Dose: One 50-mg dose daily
Dose Time: 08:00 ± 2 hours
Summary: Taken = 24 doses, Missed = 6 doses, Adherence = 80%

| Day | Date | Time | Status |
|---|---|---|---|
| Saturday | 06/15/2013 | 07:58 | Taken |
| Sunday | 06/16/2013 | 09:05 | Taken |
| Monday | 06/17/2013 | 10:01 | Missed |
| Monday | 06/17/2013 | 13:05 | Late |
| Tuesday | 06/18/2013 | 06:30 | Taken |
| Wednesday | 06/19/2013 | 08:15 | Taken |
| Thursday | 06/20/2013 | 07:45 | Taken |
| Friday | 06/21/2013 | 07:51 | Taken |
| Saturday | 06/22/2013 | 10:01 | Missed |
| Sunday | 06/23/2013 | 10:01 | Missed |
| Monday | 06/24/2013 | 10:01 | Missed |
| Tuesday | 06/25/2013 | 08:30 | Taken |
| Wednesday | 06/26/2013 | 06:15 | Taken |
| Wednesday | 06/26/2013 | 09:37 | Extra |
| Thursday | 06/27/2013 | 07:32 | Taken |
| Friday | 06/28/2013 | 07:34 | Taken |
| Saturday | 06/29/2013 | 08:12 | Taken |
| Sunday | 06/30/2013 | 09:15 | Taken |
| Monday | 07/01/2013 | 09:57 | Taken |
| Tuesday | 07/02/2013 | 07:25 | Taken |
| Wednesday | 07/03/2013 | 09:21 | Taken |
| Thursday | 07/04/2013 | 07:43 | Taken |
| Friday | 07/05/2013 | 08:09 | Taken |
| Saturday | 07/06/2013 | 05:44 | Early |
| Saturday | 07/06/2013 | 10:01 | Missed |
| Sunday | 07/07/2013 | 07:19 | Taken |
| Monday | 07/08/2013 | 10:01 | Missed |
| Tuesday | 07/09/2013 | 10:01 | Missed |
| Wednesday | 07/10/2013 | 10:01 | Missed |
| Thursday | 07/11/2013 | 07:34 | Taken |
| Friday | 07/12/2013 | 08:42 | Taken |
| Saturday | 07/13/2013 | 09:48 | Taken |
| Sunday | 07/14/2013 | 09:01 | Taken |

Referring now to FIG. 15 and FIG. 16 are perspective views of an example of a data-enabled pharmaceutical sleeve 1500 into which a conventional pharmaceutical container (e.g., the pharmaceutical container 150 shown in FIG. 5) is installed, wherein the data-enabled pharmaceutical sleeve 1500 includes the PCB assembly 112.

In this example, the data-enabled pharmaceutical sleeve 1500 includes a sleeve body 1510 that further includes a cavity 1512, an electronics compartment 1514, and optionally a battery compartment 1516. The cavity 1512 can be sized and shaped to receive any conventional pharmaceutical container. The data-enabled pharmaceutical sleeve 1500 may be formed of any suitably rigid, lightweight, and food-safe material, such as molded HDPE, e.g., molded plastic. The electronics compartment 1514 is used to house the PCB assembly 112. The battery compartment 1516 is used to house one or more batteries (not shown) for supplying power to the PCB assembly 112. An access door or panel (not shown) can be provided in the electronics compartment 1514 for accessing the PCB assembly 112. Similarly, an access door or panel (not shown) can be provided in the battery compartment 1516 for accessing the one or more batteries therein.

In the example shown in to FIG. 15 and FIG. 16, the cavity 1512 is sized and shaped to receive the pharmaceutical container 150 shown in FIG. 5. Namely, FIG. 15 shows the pharmaceutical container 150 prior to fitting into the cavity 1512 of the data-enabled pharmaceutical sleeve 1500, while FIG. 16 shows the pharmaceutical container 150 fitted into the cavity 1512 of the data-enabled pharmaceutical sleeve 1500. The cavity 1512 is sized and shaped so that the pharmaceutical container 150 is fitted snuggly therein. Additionally, the cavity 1512 is sized and shaped so that the closure 156 of the pharmaceutical container 150 is in contact with the lever 118 when present atop the container body 152. Further, the closure 156 is not in contact with the lever 118 when not present atop the container body 152.

Together, the data-enabled pharmaceutical sleeve 1500 and the conventional pharmaceutical container (e.g., the pharmaceutical container 150 shown in FIG. 5) provide substantially the same functionality as the data-enabled pharmaceutical container 100 described with reference to FIG. 1 through FIG. 14. Namely, the data-enabled pharmaceutical sleeve 1500 includes the same PCB assembly 112 and control electronics 800 as the data-enabled pharmaceutical container 100 and operates according to the method 1300 of FIG. 13 and the method 1400 of FIG. 14.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

The foregoing detailed description of embodiments refers to the accompanying drawings, which illustrate specific embodiments of the invention. Other embodiments having different structures and operations do not depart from the scope of the present invention. The term "the invention" or the like is used with reference to certain specific examples of the many alternative aspects or embodiments of the applicant's invention set forth in this specification, and neither its use nor its absence is intended to limit the scope of the applicant's invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation, as the present invention is defined by the claims as set forth hereinafter.

We claim:

1. A data-enabled pharmaceutical container, comprising:
   a) a pharmaceutical container comprising
      (i) a container body;
      (ii) a container neck; and
      (iii) a container closure, wherein the container body is configured as a reservoir for holding a quantity of medication, the container neck comprises an opening for dispensing the medication from the container body, and wherein the container closure is configured to secure the container neck opening; and
   b) an electronics module configured for sensing and tracking dose events coupled to the pharmaceutical container, wherein the electronics module comprises a housing, one or more indicators, one or more switches, and one or more sensors, and wherein one of the one or more sensors comprises a movable lever, and wherein the movable lever extends through an opening in the housing and toward the container neck, wherein the movable lever is part of a mechanism for sensing whether the container closure is present at or absent from the container neck, and wherein the movable lever is configured such that when the container closure is present on the container neck an edge of the container closure is in contact with a tip of the movable lever causing the movable lever to be in a first position, and when the container closure is not present on the container neck the edge of the container closure does not contact the tip of the movable lever causing the movable lever to be in a second position.

2. The container of claim 1 wherein medication comprises pills, capsules, or caplets.

3. The container of claim 1 wherein one or more of the one or more sensors comprise active and/or passive sensors.

4. The container of claim 1 wherein at least one of the sensors are configured to sense one or more of a presence or absence of the container closure and/or an orientation or tilt of the pharmaceutical container.

5. The container of claim 1 wherein the electronics module further comprises electrical components for processing data from the sensors with respect to a patient's predefined dosing regimen, and for storing and communicating data about doses taken, doses missed, extra doses, early doses, and/or late doses.

6. The container of claim 1 wherein one of the one or more switches comprises a momentary contact switch and wherein the movable lever in one of the first and second positions engages an actuator of the momentary contact switch.

7. The container of claim 6 wherein the movable lever and the momentary contact switch provide the sensing mechanism for determining whether the container closure of pharmaceutical container is in an opened or closed state, wherein when the container closure is present and in contact with the tip of the movable lever, a portion of the movable lever is pushed against the actuator of the momentary contact switch, and the momentary contact switch is in one state, and when the container closure is not present and not in contact with the tip of the movable lever, the movable lever is not pushed against the actuator of the momentary contact switch, and the momentary contact switch is in another state.

8. The container of claim 1 wherein the electronics module is coupled to the pharmaceutical container, such that there is no contact between the electronics module and the medication therein.

9. The container of claim 8 wherein the electronics module is coupled to the container body using a sleeve, wherein the sleeve affixes the electronics module to the container body.

10. The container of claim 1 wherein the pharmaceutical container comprises an integrated pharmaceutical container, wherein the pharmaceutical container comprises a compartment for housing the electronics module.

11. The container of claim 10 wherein the pharmaceutical container further comprises a battery compartment.

12. The container of claim 1 wherein the electronics module comprises control electronics comprising a communications interface; a processor; a real-time clock; a contact switch; a tilt sensor; and the one or more indicators.

13. The container of claim 12 wherein the processor comprises data storage for storing one or more of a patient's dosing regimen; a dose detection algorithm; and actual dose data.

14. The container of claim 12 wherein the control electronics are configured for providing a reminder at dose time, detecting valid dose events, and processing and communicating data about dose events and/or dose exception events.

15. The container of claim 4 wherein the at least one of the sensors comprise a tilt sensor.

16. The container of claim 15 wherein the tilt sensor senses when the container body is in a tilted state exceeding a threshold angle from a first position.

17. The container of claim 16 wherein the threshold angle is in the range of about 45° to about 90°.

18. The container of claim 15 wherein the tilt sensor comprises any one of an on/off tilt sensor, an accelerometer, an inertial measurement unit (IMU), or an inclinometer.

19. The container of claim 1 wherein sensing a valid dose event requires data input from at least two of the one or more switches and/or sensors to coincide with one another.

20. The container of claim 19 wherein the coinciding at least two data inputs from the one or more switches and/or sensors comprises data input indicating the container closure is not present on the container neck and the container body is in a tilted state exceeding a threshold angle from a first position.

21. The container of claim 1 wherein the one or more indicators comprise light-emitting diodes (LED).

22. The container of claim 1 wherein the electronics module is further configured for providing a dose reminder and communicating valid dose events and/or dose exception events.

23. The method of claim 1 wherein the electronics module further comprises a printed circuit board (PCB) assembly housed within the housing, the PCB assembly comprising a PCB.

* * * * *